United States Patent [19]

Kerr

[11] E Re. 30,430

[45] Reissued Nov. 4, 1980

[54] CATALYST TREATMENT

[75] Inventor: Ralph O. Kerr, Bloomington, Ind.

[73] Assignee: Denka Chemical Corporation, Houston, Tex.

[21] Appl. No.: 14,833

[22] Filed: Feb. 26, 1979

Related U.S. Patent Documents

Reissue of:

[64] Patent No.: 4,006,168
Issued: Feb. 1, 1977
Appl. No.: 563,740
Filed: Mar. 31, 1975

[51] Int. Cl.[3] ..... C07D 307/60

[52] U.S. Cl. ..... 260/346.75; 260/346.4; 562/547; 252/411 R

[58] Field of Search ..... 260/346.75, 346.4; 252/411 R; 562/547

[56] References Cited

U.S. PATENT DOCUMENTS

| | | | |
|---|---|---|---|
| 2,885,409 | 5/1959 | Ryder | 260/346.8 |
| 3,074,969 | 1/1963 | Kerr et al. | 260/346.75 |
| 3,236,782 | 2/1966 | Koch | 252/411 |
| 3,882,159 | 5/1975 | Callahan et al. | 260/465.3 |

*Primary Examiner*—Henry R. Jiles
*Assistant Examiner*—Bernard Dentz
*Attorney, Agent, or Firm*—Kenneth H. Johnson

[57] ABSTRACT

Molybdenum - vanadium - oxygen oxidation catalyst for producing maleic anhydride from benzene is regenerated and stabilized by the addition of a compound of Mo, Ni, Co, Mn or U, preferably a volatile compound, to the catalyst, after a decline in activity.

13 Claims, No Drawings

CATALYST TREATMENT

Matter enclosed in heavy brackets [ ] appears in the original patent but forms no part of this reissue specification; matter printed in italics indicates the additions made by reissue.

BACKGROUND OF THE INVENTION

This invention relates to improvements in the preparation of dicarboxylic acid anhydrides by the vapor phase oxidation of hydrocarbons and more particularly relates to improvements in the process for the catalytic oxidation of hydrocarbons to dicarboxylic anhydrides in the presence of a vanadium-molybdenum-oxygen catalyst.

It has recently been discovered that high yields of dicarboxylic anhydrides may be obtained by oxidizing hydrocarbons in the vapor phase in contact with a vanadium-molybdenum-oxygen catalyst. Although high yields of dicarboxylic anhydrides have been obtained by such processes, it has been found that the yield of product diminishes with time. It is an object of this invention to provide a method whereby the catalyst may be reactivated and whereby the high yields may be maintained. It has been found as part of the present invention that one reason for the decrease in yield is the deactivation of a portion of the catalyst particles. It is also an object of this invention to selectively activate the deactivated catalyst particles without impairing the activity of the remaining catalyst particles.

SUMMARY OF THE INVENTION

Briefly stated, the present invention is the discovery that vanadium-molybdenum-oxygen catalysts may be reactivated and stabilized by adding to the catalyst, compounds of molybdenum, nickel, cobalt, manganese, or uranium and mixtures thereof. More particularly, volatile or volatizable compounds of molybdenum, nickel, cobalt, manganese, uranium or mixtures, are preferably employed.

DETAILED DESCRIPTION OF THE INVENTION

Both organometallic compounds and inorganic compounds of Mo, Ni, Co, Mn and U may be used according to the present invention. Suitable organometallic compounds include molybdenum acetylacetonate, mesitylenemolybdenum tricarbonyl, nickel dimethyl glyoxime, dicyclopentadienyl nickel, cobalt (II) formate, (tert-butylcyclopentadienyl) manganese tricarbonyl, (ditert-butylcyclopentadienyl) manganese tricarbonyl, uranium (V) ethoxide, uranium isopropoxide and the like.

There are a number of inorganic compounds, which are suitable for the present invention including molybdenum dibromide, molybdenum tetrabromide, molybdenum tribromide, molybdenum carbonyl, molybdenum pentachloride, molybdenum tetrachloride, molybdenum trichloride, molybdenum hexafluoride, molybdenum oxytetrachloride, molybdenum oxytrichloride, molybdenum oxytrichloride, molybdenum oxypentachloride, molybdenum oxytetrafluoride, nickel acetate, nickel carbonyl, nickel nitrate hexahydrate, cobalt nitrosyl carbonyl, manganese nitrate, uranium hexafluoride, uranium tribromide, uranyl nitrate and the like.

Suitable Mo, Ni, Co, Mn and U compounds will generally have a boiling or volatilization temperature of no greater than 250° C. and preferably no greater than 200° C.

According to the present process, the volatilized Mo, Ni, Co, Mn or U compound is preferably added to the hydrocarbon reaction stream being fed over the vanadium - molybdenum - oxygen catalyst. Although it is not necessary to continue the oxidation of the hydrocarbon and the production of the maleic anhydride, it is a particular advantage of the present process that it may be carried out without interruption of the reaction.

The regeneration process of the present invention may be initiated at any time a decline in the activity of the catalyst is noted, usually by a decline in the yield from the process or an increase in the temperature of the hot spot in the catalyst bed. An increase in the temperature of the hot spot may require reduction in the hydrocarbon throughput, thereby also reducing the unit yield.

The vanadium-molybdenum-oxygen catalysts are well known and have been described and used for the preparation of maleic anhydride in numerous patents; for example, U.S. Pat. Nos. 1,636,857; 2,294,130; 2,674,582; 2,885,409; 2,967,185; 3,074,969; 3,163,613; and 3,211,671.

The vanadium-molybdenum-oxygen catalysts to be reactivated according to the present invention, appear to comprise vanadium, molybdenum and oxygen combined in a complex. Suitable catalyst may have overall atomic ratios of molybdenum to vanadium in the range of 0.05 to 0.95:1. The vanadium-molybdenum-oxygen catalyst may contain various stabilizers and modifiers such as nickel, cobalt, iron, manganese, phosphorus, and alkali and alkaline earth metals, generally in percents of less than 25 weight percent based on the total weight of vanadium and molybdenum. For example, the vanadium-molybdenum-oxygen catalyst may be modified with 0.002 to 0.1 atom of nickel, 0.0053 to 1.106 atom of cobalt, 0.0072 to 0.30 atom of iron, 0.0003 to 0.12 atom of phosphorus and/or 0.011 to 0.76 atom of lithium, sodium, potassium, calcium or strontium per atom of vanadium. The atomic ratio of oxygen to the remaining components of the catalyst, when the catalyst is in the process of being used to catalyze the oxidation is difficult to determine and is probably not constant due to the competing reactions of oxidation and reduction taking place during the reaction at high temperatures. The overall ratio of oxygen to the combined atoms of vanadium and molybdenum at room temperature would be such as about 4 to 10 atoms of oxygen per the combined atoms of vanadium and molybdenum. At any rate the catalyst is present during the reaction as an oxide of vanadium and molybdenum.

The vanadium-molybdenum-oxygen catalyst may be prepared in a number of ways, as shown in the art. The catalyst may be prepared by precipitating the vanadium and molybdenum compound, either with or without a carrier, from a colloidal dispersion of the ingredients in an inert liquid. The catalyst may also be prepared by dissolving vanadium and molybdenum compounds in a common solvent, such as hot oxalic acid and thereafter depositing the solution on a carrier. In some instances, the catalyst may be deposited as molten metal compounds on a carrier; however, care must be taken not to vaporize off any of the ingredients. The catalyst may also be prepared by heating and mixing anhydrous forms of molybdenum acids with vanadium compounds.

In one particular method of catalyst preparation the desired amount of molybdenum oxide is introduced by dissolving ammonium molybdate in concentrated hydrochloric acid. Then, the desired amount of ammomium vanadate was dissolved in the solution. The other components, if any, are dissolved in the acid solution, for example, cobalt nitrate, nickel nitrate, sodium chloride, trisodium phosphate and the like. The resulting solution of the mixture of compounds is mixed with granules of ceramically bonded, fused porous alumina, and subjected to evaporation, resulting in the deposition of the catalytic materials on the surface in the pores of the support or carrier. The catalyst-carrier is then calcined in the presence of air in a kiln held at a constant temperature of 650°-800° F.

The process of oxidation described herein is applicable generally to processes for the oxidation of hydrocarbons, e.g., having four to eight carbon atoms, to dicarboxylic [acids] *anhydrides* in the presence of vanadium-molybdenum-oxygen catalysts. However, the process is particularly applicable to processes for the preparation of maleic anhydride, from $C_4$ hydrocarbons and benzene, and especially the preparation of maleic anhydride from benzene, [terephthalic] *phthalic* anhydride from ortho xylene and paraphthalic anhydride from paraxylene. The oxidation of the hydrocarbon to aliphatic dicarboxylic anhydrides may be accomplished by contacting low concentrations of hydrocarbon in oxygen in contact with the vanadium-molybdenum-oxygen catalyst. Air is the most economical source of oxygen, but mixtures of oxygen and diluent gases, such as nitrogen may also be employed. Air streams enriched with oxygen may also be used. The gaseous feed stream to the reactor normally will contain about 1.1 to about 1.6 mol percent hydrocarbons based on the total gaseous stream. About 1.25 to about 1.5 mol percent of the hydrocarbon generally gives optimum output of product, although higher and lower concentrations may be utilized. The flow rate of the gaseous stream to the reactor may be varied within fairly wide limits, but a preferred range is at the rate of about 50 to 200 grams of hydrocarbon per liter of catalyst per hour, and generally will be within the range of about 75 to 150 grams of hydrocarbon per liter of catalyst per hour. Residence time of the gas stream will normally be less than about 5 seconds, such as from about 0.01 to less than 2 seconds. The best results have been obtained at residence times of less than 1 second. The flow rates and residence times are calculated at standard conditions of 760 mm. of mercury and at 25° C. The preferred hydrocarbon feed in benzene.

The temperature of reaction for the oxidation of the hydrocarbon to dicarboxylic anhydrides may be varied. The temperature of reaction will depend to some extent upon the size of the reactor, the hydrocarbon concentration and the particular vanadium-molybdenum-oxygen catalyst being employed. A suitable temperature of reaction is from about 340° to about 500° C., as measured at the maximum temperature in the reactor. Better results have been obtained at temperatures from 360° to 475° C. The pressure on the reactor is not generally critical, and the reaction may be conducted at atmospheric, superatmospheric, or below atmospheric pressure.

The oxidation of the hydrocarbons to dicarboxylic anhydrides in the presence of a vanadium-molybdenum-oxygen catalyst may be conducted in a variety of reactors. Fixed bed reactors used for the production of maleic anhydride are quite satisfactory. Multiple tube heat exchanger type reactors have been successfully used. Because the reaction is exothermic, the heat generated must be conducted away from the reactor. Normally, the reactors contain a preheat zone of an inert material.

Catalyst support may be used to give the catalyst physical strength and stability. The carrier may vary in size but generally is from about 2½ mesh to about 10 mesh in the Tyler Standard Screen Size. Useful carriers are such as the inert alumina carriers or the silicon carbides. The amount of the vanadium-molybdenum-oxygen catalysts on the carrier is usually in the range of about 10 to about 35 weight percent of the total weight of complex plus carrier. The final particle size of the catalyst particles will also preferably be about 2½ to about 10 mesh size. The final catalyst particles may be of a variety of shapes, with the preferred shape being the shape of cylinders or spheres or irregular spheres. Inert diluents such as silica may be present in the catalytic surface, but the combined weight of the vanadium, molybdenum and oxygen will preferably be at least 50 weight percent of the catalytic surface.

The activating compounds can be added to the vanadium-molybdenum-oxygen catalysts in a number of different ways. The vanadium-molybdenum-oxygen catalyst will first be used for the oxidation of hydrocarbons to dicarboxylic anhydride for a period of time until the yield of dicarboxylic anhydride diminishes. The molybdenum compound may then be added to reactivate the catalyst. The reactivation step may be accomplished either with or without the flows of hydrocarbon and/or oxygen continued.

A preferred method for the reactivation of the vanadium-molybdenum-oxygen catalyst is by the continuous or intermittent addition of volatile inorganic molybdenum compound to the gaseous stream of hydrocarbons and oxygen-containing gases entering the reactor. By such a technique, the activity of the vanadium-molybdenum-oxygen catalyst is maintained through continuous reactivation or stabilization. An advantage of this procedure is that the production of dicarboxylic anhydride does not have to be interrupted.

Still another method for the addition of the molybdenum compound to the vanadium-molybdenum-oxygen catalyst is by the addition of the molybdenum compound in liquid phase by pouring the molybdenum compound over the catalyst to be reactivated. Reactivation by this technique may suitably be performed at about room temperature if desired.

Thus, the molybdenum compound may be added to the vanadium-molybdenum-oxygen catalyst by a variety of methods such as adding the molybdenum compound as a liquid or gas. Other techniques such as the use of an aerosol to convey the molybdenum compound are also satisfactory. Suspensions or colloidal solutions of the molybdenum compounds may be employed. Solvents for the molybdenum compound may be included. The molybdenum compound may be added such as to the hydrocarbon, the oxygen containing gas or via a diluent gas such as nitrogen. The overall temperature range for the addition of the molybdenum compound suitably will be from about 0° to 600° C., depending upon the particular compound selected. However, the preferred temperature of the vanadium-molybdenum-oxygen catalyst at the time of addition of the molybdenum compound will be at least 325° C. with still better results being obtained at a catalyst temperature of at least 375° C. The upper limits of the temperature of the catalyst during reactivation will suitably be about 450° or 500° C., or perhaps higher for momentary periods of time. The pressure during the addition may be atmospheric, sub-atmospheric or super-atmospheric. The conditions of concentration, temperature and pressure should be adjusted to permit optimum contact of the molybdenum compound with the vanadium-molybdenum-oxygen catalyst.

The amount of molybdenum compound added may be varied depending upon such factors as the age of the catalyst, the temperature at which the catalyst has been operated, the composition of the vanadium-molybdenum-oxygen catalyst and so forth. When the molybdenum compound is continuously added to the gaseous stream entering the reactor, the quantity is generally relatively small such as at least about 0.000005 mol of molybdenum compound added per gram atom of vanadium in the catalyst per day, such as at an average rate of 0.00002 gram mol per day per gram atom of vanadium, or based on the hydrocarbon entering the reactor about 0.0000001 to 0.00001 mol of the molybdenum compound per mol of hydrocarbon. Preferred amounts are about 0.000001 to 0.000008 mol of the molybdenum compound per mol of the hydrocarbon such as benzene. As pointed out above, the addition may be either intermittent or continuous. Of course, even if the molybdenum compound is added continuously, it is not necessary that it be added at a constant rate.

It has been found that by utilizing the process of this invention the deactivated catalyst particles are selectively activated. Another advantage of the invention is that a fixed catalyst bed containing a preheat zone of inert particles may be activated without removing the preheat zone or the catalyst particles from the reactor. The reactivation procedure does not cause the catalyst bed to be plugged.

In a preferred method the activating compound is added to the hydrocarbon flow intermittently in the amount of 0.000002 to 0.0002 gram mole of molybdenum, nickel, cobalt, manganese or uranium compound (or mixtures) per gram mole of vanadium in the catalyst and more preferably in the amount of 0.00001 to 0.0001 gram mole per gram mole of vanadium.

The present invention may be employed with a vanadium-molybdenum-oxygen catalyst which has been pretreated with a phosphorus compound prior to the Mo, Ni, Co, Mn or U activator-regenerator treatment. It is believed that the phosphorus compound selectively deactivates some portions of the catalyst to a very slight extent, in a manner, beneficial to the subsequent reactivation with inorganic molybdenum, nickel, cobalt, manganese or uranium compounds. Suitable phosphorus compounds are phosphorus halides of the structure $PX_n'$ wherein X' is Cl, Br, I or F and n is 3–5 or an organophosphorus compound selected from the group consisting of

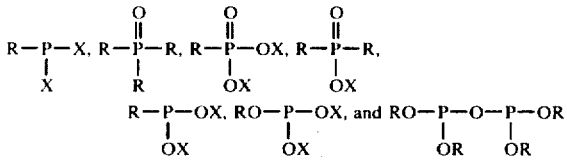

wherein R is phenyl or an alkyl radical of one to 6 carbon atoms and X is H or R. Sulphur may be substituted for oxygen in any of these formulas. Suitable compounds are such as the primary, $RPH_2$, secondary, $R_2PH$, and tertiary, $R_3P$, phosphines such as ethyl phosphine; the tertiary phosphine oxides, $R_3PO$, such as tripropyl phosphine oxide; and primary, $RP(O)(OX)_2$, and secondary, $R_2P(O)OX$, phosphonic acids such as benzene phosphonic acid; the esters of the phosphonic acids such as diethyl methane-phosphonate; the phosphonous acids, $RPO_2X_2$, such as benzene-phosphonous acid and the esters thereof such as the monoethyl ester; the phosphonous acids, $R_2POX$, such as diethyl phosphonous acid and the esters thereof such as the monoethyl ester; the primary, $ROP(OX)_2$, secondary, $(RO)_2POX$, and tertiary, $(RO_3)P$, phosphites such as diethyl phosphite, trimethyl phosphite, triethyl phosphite, triisopropyl phosphite, tripropyl phosphite and tributyl phosphite, and the pyrophosphites such as tetraethyl pyrophosphite. Suitable phosphorous compounds are such as phosphorus trichloride, phosphorus trifluoride, phosphorus dichloride monofluoride, phosphorus tribromide, phosphorus dibromide trichloride, phosphorus dibromide trifluoride, phosphorus triiodide, phosphorus pentachloride, the diphosphorus halides, e.g., phosphorus dichloride ($P_2Cl_4$), phosphorus diiodide ($P_2I_4$), the primary, $RPH_2$, secondary, $R_2PH$, and tertiary, $R_3P$, phosphines such as ethyl phosphine; the tertiary phosphine oxides, $R_3PO$, such as tripropyl phosphine oxide; the primary, $RP(O)(OX)_2$, and secondary, $R_2P(O)OX$, phosphonic acids such as benzene phosphonic acid; the esters of the phosphonic acids such as diethyl methane-phosphonate; the phosphonous acids, $RPO_2X_2$, such as benzenephosphonous acid and the esters thereof such as the monoethyl ester; the primary, $ROP(OX)_2$, secondary, $(RO)_2POX$, and tertiary, $(RO_3)P$, phosphites such as diethyl phosphite, trimethyl thiophosphite, triethyl phosphite, triisopropyl phosphite, tripropyl phosphite and tributyl phosphite, and the pyrophosphites such as tetraethyl pyrophosphite. Preferred phosphorus compounds are those wherein the phosphorus has a valence of less plus five. The phosphorus compounds will suitably have a boiling point of no greater than 250° C. and preferably will have a boiling point of no greater than 200° C. and may be added to the vanadium-molybdenum-oxygen catalyst by the same means as the Mo, Ni, Co, Mn or U compounds as described above.

The phosphorus compound may be added up to 0.0012 gram mole per gram mole of vanadium in the vanadium-molybdenum-oxygen catalyst and generally in the range of 0.00004 to 0.0008 gram mole per gram mole of vanadium.

In a preferred embodiment, as disclosed for the addition of the Mo, Ni, Co, Mn or U compounds, the phosphorus compound used is preferably one which is volatile or will volatilize under the conditions of addition to the hydrocarbon flow, such as, trimethyl phosphite, phosphorus trichloride, triethyl thiophosphate, phosphorus pentafluoride and phosphorus dichloride monofluoride.

EXAMPLE 1

Benzene was oxidized to maleic anhydride in a 1.06 inch carbon steel, twelve foot long reactor. The reactor was cooled by a salt bath. A mixture of 1.35 mol percent benzene in air was fed to the reactor. The flow rate was 92.4 grams of benzene per liter of catalyst per hour. The catalyst comprised an oxide of vanadium and molybdenum. The actives were supported on an inert carrier.

The catalyst gave a maximum yield of 88.2 weight percent maleic anhydride after 1400 hours at a throughput of 9.06 pounds of benzene per tube per day. The reactor temperature at this time was maintained in the range of 360° to 410° C. After 9200 hours of operation the yield had dropped to 72.9 weight percent maleic anhydride, together with an increased amount of CO and $CO_2$. After 9300 hours of operation, the catalyst was reactivated. To the benzene-air feed stream was added 0.05 liters per minute of trimethyl phosphite and then phosphorus trichloride. A total 2000 ml. each of $(CH_3O)_3P$ and $PCl_3$ was added in this manner over a 2 hour period. After a 2 hour period during which the reaction continued 2 lb. of $MoF_6$ was added over a 0.5 hour period. After 9600 total hours of operation the yield of maleic anhydride was 80.4 wt. percent, and the percent CO and $CO_2$ had dropped significantly. After 9900 total hours of operation, an additional 2000 ml. of phosphorus trichloride was added in the same manner as the original addition followed by 1 lb. of $MoF_6$ to reactivate the catalyst. After 10200 total hours of operation an additional 1000 ml. of $PCl_3$ was added in the same manner followed by 1 lb. $MoF_6$ to again reactivate the catalyst. After 10600 hours of operation the catalyst was producing a yield of 81.7 weight percent maleic anhydride.

The addition of Ni, Co, Mn and U compounds to the reaction stream in the same manner as described for molybdenum, either alone or in combination with molybdenum compounds or each other, show some degree of improvement or regeneration in a vanadium-molybdenum-oxygen catalyst which has declined in activity.

The invention claimed is:

1. In a process for the vapor phase oxidation of $C_4$ to $C_8$ hydrocarbons to dicarboxylic [acids] *anhydrides* wherein said hydrocarbon is contacted with a vanadium-molybdenum-oxygen catalyst wherein said catalyst gradually decreases in activity, the improvement comprising adding to said catalyst, after said decrease in activity, *a compound of a phosphorus halide or an organophosphorus compound selected from the group consisting of*

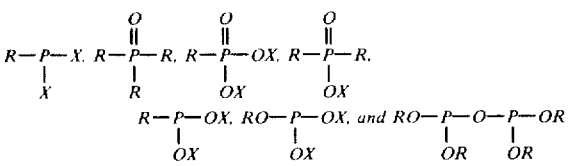

*wherein R is phenyl or an alkyl radical of one to 6 carbon atoms and X is H or R, and thereafter adding to said catalyst* a volatilized compound of molybdenum, nickel, cobalt, manganese, uranium or mixtures thereof.

2. The process according to claim 1 wherein said compound *of molybdenum, nickel, cobalt, manganese, uranium, or mixtures thereof* has volatilization temperature of 250° C. or less.

3. The process according to claim 1 wherein said compound *of molybdenum, nickel, cobalt, manganese, uranium, or mixtures thereof* is an inorganic molybdenum compound.

4. The process according to claim 3 wherein said inorganic compound is molybdenum dibromide, molybdenum tetrabromide, molybdenum tribromide, molybdenum carbonyl, molybdenum pentachloride, molybdenum tetrachloride, molybdenum trichloride, molybdenum hexafluoride, molybdenum oxytetrachloride, molybdenum trichloride, molybdenum oxypentachloride or molybdenum oxytetrafluoride.

5. The process according to claim 4 wherein said inorganic compound is molybdenum hexafluoride.

6. The process according to claim [3] *1* wherein said [inorganic] compound is molybdenum dibromide, molybdenum tetrabromide, molybdenum tribromide, molybdenum carbonyl, molybdenum pentachloride, molybdenum tetrachloride, molybdenum trichloride, molybdenum hexafluoride, molybdenum oxtetrachloride, molybdenum oxytrichloride, molybdenum oxypentachloride, molybdenum oxytetrafluoride, nickel acetate, nickel carbonyl, nickel nitrate hexahydrate, cobalt nitrosyl carbonyl, manganese nitrate, uranium hexafluoride, uranium tribromide or [manyl] *uranyl* nitrate.

7. The process according to claim 1 wherein said catalyst has an atomic ratio of molybdenum to vanadium in the range of 0.05 to 0.95 to 1.

[8. The process according to claim 1 wherein prior to adding said inorganic compound to said catalyst, a compound of a phosphorus halide or an organo-phosphorus compound selected from the group consisting of

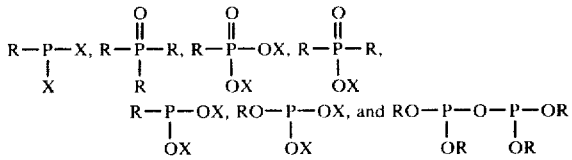

wherein R is phenyl or an alkyl radical of one to 6 carbon atoms and X is H or R, is added to said catalyst.]

9. The process according to claim [8] *1* wherein said phosphorus compound is volatilizable.

10. The process according to claim [8] *1* wherein said inorganic compound is molybdenum hexafluoride.

11. The process according to claim 1 wherein said compound *of molybdenum, nickel, cobalt, manganese, uranium or mixtures thereof* is added to said catalyst during the vapor phase oxidation of hydrocarbons to produce dicarboxylic [acids] *anhydrides.*

12. The process according to claim 1 wherein said hydrocarbons have 4 to 6 carbon atoms and said maleic anhydride is the principal product.

13. The process according to claim 12 wherein the hydrocarbon is benzene.

14. In a process for oxidizing benzene to maleic anhydride which comprises contacting a vaporous stream of benzene with a vanadium-molybdenum-oxygen catalyst, wherein the yield of maleic anhydride diminishes with time, the improvement comprising adding *a volatilized compound of a phosphorus halide or an organo-phosphorus compound selected from the group consisting of*

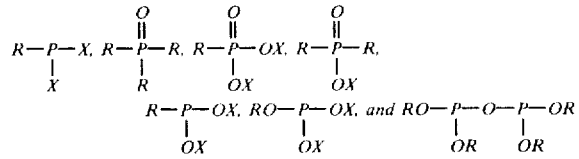

*wherein R is phenyl or an alkyl radical of one to 6 carbon atoms and X is H or R, followed by adding* a volatilized inorganic molybdenum compound to said vaporous stream of benzene while maintaining said catalyst at a temperature of 340° to 500° C.

* * * * *

UNITED STATES PATENT AND TRADEMARK OFFICE

CERTIFICATE OF CORRECTION

PATENT NO. : Re. 30,430

DATED : November 4, 1980

INVENTOR(S) : Ralph O. Kerr

It is certified that error appears in the above—identified patent and that said Letters Patent is hereby corrected as shown below:

Column 8, line 38 reads "inorganic compound is" but should read -- compound is --

Signed and Sealed this

*Twenty-second* Day of *September 1981*

[SEAL]

*Attest:*

GERALD J. MOSSINGHOFF

*Attesting Officer*

*Commissioner of Patents and Trademarks*